United States Patent [19]
Ryan

[11] Patent Number: 5,250,438
[45] Date of Patent: Oct. 5, 1993

[54] METHOD FOR DIFFERENTIAL DETERMINATION OF WHITE BLOOD CELLS USING DIAZOLIDINYL UREA TO STABILIZE WHITE BLOOD CELLS

[75] Inventor: Wayne L. Ryan, Omaha, Nebr.

[73] Assignee: Streck Laboratories, Inc., Omaha, Nebr.

[21] Appl. No.: 520,884

[22] Filed: May 9, 1990

[51] Int. Cl.$^5$ .............................. G01N 33/48
[52] U.S. Cl. ........................ 436/17; 436/10; 436/18; 436/63
[58] Field of Search ............. 436/63, 164, 172, 900, 436/10, 17, 18; 422/77; 424/3

[56] References Cited

U.S. PATENT DOCUMENTS

| | | | |
|---|---|---|---|
| 4,185,964 | 1/1980 | Lancaster | 436/10 X |
| 4,286,963 | 9/1981 | Ledis et al. | 436/18 |
| 4,303,408 | 12/1981 | Kim et al. | 422/56 |
| 4,346,018 | 8/1982 | Carter et al. | 436/17 |
| 4,528,274 | 7/1985 | Carter et al. | 436/10 |
| 4,637,986 | 1/1987 | Brown et al. | 436/10 |
| 4,745,071 | 5/1988 | Lapicola et al. | 436/18 X |
| 4,882,284 | 11/1989 | Kirchanski et al. | 436/63 |
| 5,008,202 | 4/1991 | Edmondson et al. | 436/18 |
| 5,039,487 | 8/1991 | Smith | 422/56 |

Primary Examiner—Jill A. Johnston
Assistant Examiner—Arlen Soderquist
Attorney, Agent, or Firm—Tilton, Fallon, Lungmus & Chestnut

[57] ABSTRACT

A new method for separation of white cells in differential hematology instruments is described. In the method described, white cell shrinkage is controlled by the use of diazolidinyl urea and accelerated with alcohol thereby providing a reproducible method for easy manipulation of the white cells. In addition, it was found that adsorption of blood platelets and red blood cells in the instruments can be prevented by use of a surfactant such as the polyols.

7 Claims, 4 Drawing Sheets

ND FOR DIFFERENTIAL
METHOD FOR DIFFERENTIAL DETERMINATION OF WHITE BLOOD CELLS USING DIAZOLIDINYL UREA TO STABILIZE WHITE BLOOD CELLS

BACKGROUND OF THE INVENTION

This invention relates to methodology and an improved diluent system for use in the differentiation of leukocytes.

The use of instrumentation to count red blood cells and white blood cells has been available for close to 30 years. The earliest instruments and the most modern require a lysing agent which hemolyzes the red blood cells so that the white blood cells can be counted. A variety of lysing agents have been used which differ in their rate of hemolysis and their effect on the white blood cells.

A. Hatch and T. Balazs in the *American Journal of Clinical Pathology*, Vol. 36, No. 3, pp. 220-223, 1961, describe the use of acetyltrimethyl ammonium bromide, saponin and Triton ® to lyse red blood cells and produce white blood cell (WBC) distribution. It is important that the authors noted that different sized leucocytes can be observed. They were able only to get a "rough estimate of the different types of white cells present". Their comments are of interest:

"Distribution of cell sizes were easily obtained but, inasmuch as there was a large amount of overlapping in size and type of cell they indicated only a rough estimate of the different types of white cells present. A differential stromatolysing agent would be required for a true differential picture. Akeroyd and associates report that the initial decrease in white cell counts using Triton ® is owing to lysis of the lymphocytes. If this is true, it should be possible to perform differential blood counts on the electronic counter."

The authors clearly saw the need for adjustment of the lysing agent to obtain several populations of white cells.

Several years later in 1974, Hughes-Jones et al described in the *Journal of Clinical Pathology*, Vol. 27, pp. 623-625, preparation of an analysis system that distinguished neutrophiles and lymphocytes in blood. They used saponin to lyse the red cells and to separate the WBC but pointed out the difficult of adjusting the concentration of lysing agent.

P. A. Wycherley and M. J. O'Shea in the *Journal of Clinical Pathology*, Vol. 31, pp. 271-274, 1978 reported further development of the method by linking a Coulter Channelyzer ® to a Coulter Model S ® cell counter. They were able to standardize the lysing solution and the method of analysis. The extension of the earlier studies to include a third population of cells was reported by Ledis et al in U.S. Pat. No. 4,485,175 where they used a mixture of alkyl ammonium chloride surfactants and added them slowly, and at a dilute concentration, to lyse the red cells and produce WBC separation. Procaine is added to stabilize the white cells. The authors point out that the quaternary ammonium compounds vary in composition and purity and, therefore, that it is necessary to adjust the concentration of lysing agent to accommodate this problem.

Matsuda and Shinkai in U.S. Pat. No. 4,656,139 reported a similar system using quaternary ammonium lysing agents with citric acid and a diluent containing a boric acid buffer. The citric acid shrinks the red cell ghosts so that they do not interfere with the WBC count.

In U.S. Pat. No. 4,745,071 a single quaternary ammonium surfactant is used instead of a mixture. The use of dodecyltrimethyl ammonium chloride is claimed to give the gentle red cell lysis required, and provides a uniquely selective effect on the leucocytes. This surfactant was previously used in admixture with other quaternary ammonium surfactants.

The only method with a considerably different approach is that described by Brown and Kirchanski in U.S. Pat. No. 4,637,986. According to this method, an organic buffer and leukoprotective agents at a pH of 8.5 are employed to produce a differential white cell count.

The above investigations show only slight differences in approach. All of them indicate the need for a surfactant, usually a quaternary ammonium salt, and the careful adjustment of the concentration. This careful adjustment was evident to the early investigators, and this is necessary because variation in strength and purity of the agents affects the lysing action of the surfactant.

Needless to say, the search for a red blood cell lysing procedure for separating and counting white blood cells which removes the necessity of careful adjustments continues.

It is an object of the invention to provide an improved method for differentiating leukocytes (white blood cells) in whole blood by the lysing of red blood cells therein which method does not require careful adjustments.

It is also an object of the invention to provide a more reliable method for the lysis of red blood cells for differentiation of white blood cells.

Yet another object of the invention is to provide a novel method of stabilizing white blood cells during the lysis of blood cells.

A further object of the invention is to provide a novel diluent for use in diluting whole blood samples to be mixed with lysing agents for the volumetric differentiation of white blood cells.

Another object of the invention is to provide novel reagents which make it possible to use a single diluent and lysing agent in most of the differential instruments available (e.g., Coulter ® S Series, Sequoia-Turner ® 2000, 1600, 1500 and Baker ® 900).

SUMMARY OF THE INVENTION

It has been discovered that the compound diazolidinyl urea stabilizes white blood cells, to such an extent that wide variations in the concentrations and types of lysing agents are possible.

Thus, as one embodiment, the invention provides an improved blood diluent having a predetermined pH and osmolality for diluting whole blood samples to be mixed with a lysing agent for the volumetric differentiation of white blood cells, comprising an aqueous solution of organic buffer and a white blood cell stabilizer, the improvement comprising employing as said white cell stabilizer diazolidinyl urea.

In another embodiment of the invention, the diluent includes a surfactant in an amount sufficient to reduce adsorption of blood platelets and red blood cells in hematology analyzing instruments that have surfaces that tend to adsorb same during analysis. Unless this adsorption is prevented it can lead to erratic low platelet counts and low red cell counts. The addition of a surfactant solves this problem.

Another aspect of the invention involves providing an improved method for the differentiation of white blood cells in whole blood using differential hematology analyzing instruments wherein a whole blood sample is diluted with a diluent containing a white cell stabilizer and mixed with a lysing agent to lyse the red blood cells and differentiate the white blood cells, the improvement comprising using as said white blood cell stabilizer diazolidinyl urea in an amount sufficient to stabilize said white blood cells against shrinkage during said lysis.

In yet another aspect of the invention, the lysis is effected using a novel lysing agent comprising an aqueous solution of quaternary ammonium salt, a lower alkanol and water, said lower alkanol being present in an amount that accelerates the shrinking effect of the quaternary ammonium salt. Use of the combination of the diazolidinyl urea and alkanol provides easy manipulation of the white cells and a highly reproducible method for separating white blood cells. For instance, in the production of large quantities of the diluent of the invention, it is possible for too much diazolidinyl urea to have been added in which case the granulocytes would appear too far to the right on the histogram, that is, increase in size. By adding or increasing the alcohol in the lyse, the position of these white blood cells can be slightly altered so as to more accurately place them. In other words, the combination of diazolidinyl urea and alkanol permits movement in both directions and therefore greater control.

DETAILED DESCRIPTION OF THE INVENTION

The Diluent

Figure 1:
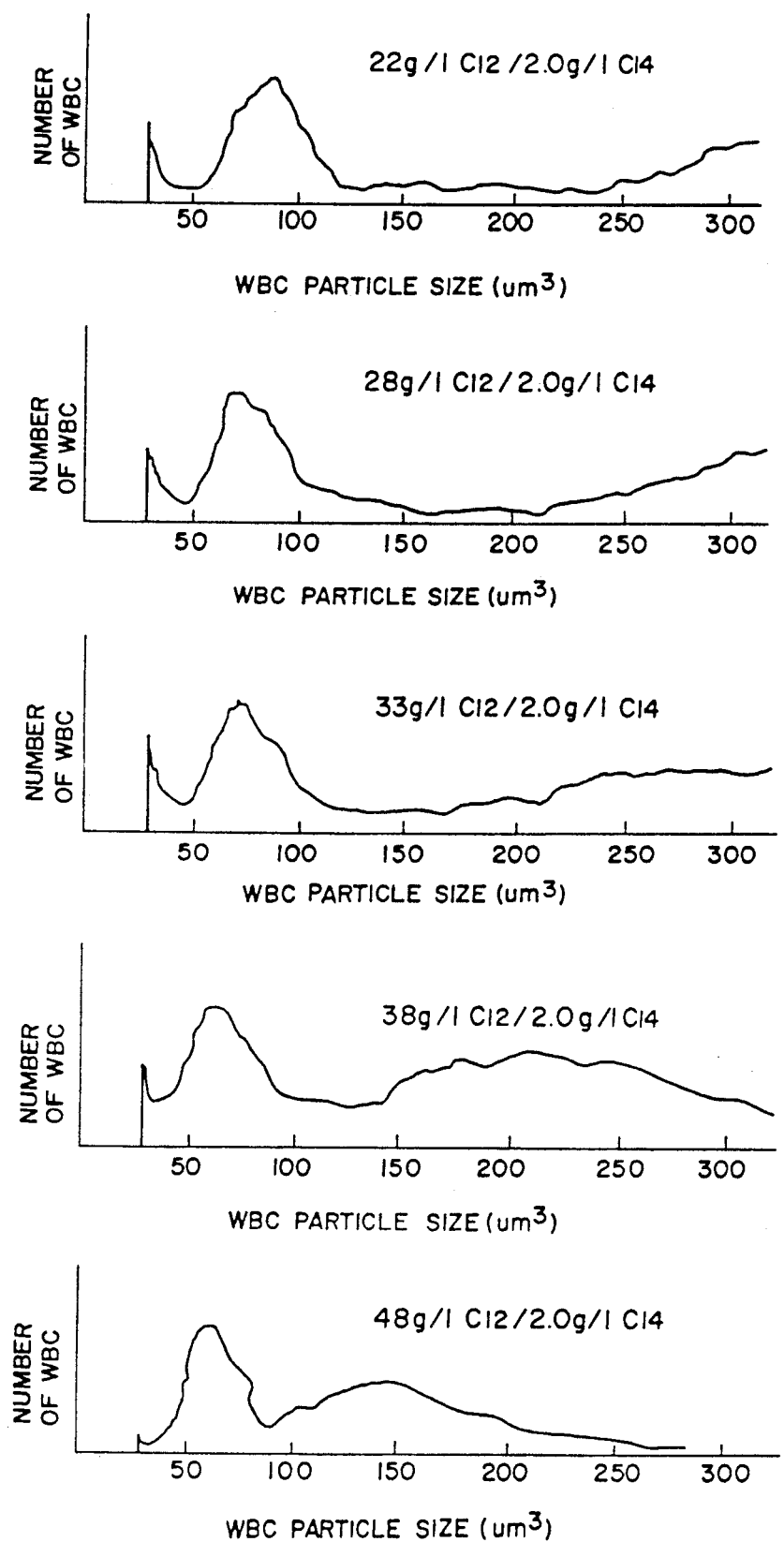
FIG. 1 shows the effect of the lysing agent concentration on the position of the white blood cells.

The improved isotonically balanced diluent of the invention comprises an aqueous solution of an organic buffer, an inorganic salt to correct ionic strength and osmolality in the whole blood sample, an additional alkali salt for pH optimization and diazolidinyl urea as the white cell stabilizer so as to maintain the volume of the red blood cells and white blood cells. Except for the diazolidinyl urea, all of the components of the diluent of the invention are those often employed in prior art diluent systems.

Illustrative of suitable organic buffers are: ADA [N-(2-acetamido)-2-iminodiacetric acid; N-(carba-moylmethyl)iminodiacetic acid], MOPS [3-(N-Morpholino)propanesulfonic acid], PIPES [piperazine-N,N'-bis(2-ethanesulfonic acid); 1,4-piperazinediethanesulfonic acid], HEPES [N-(2-hydroxyethyl)piperazine-N'-(2-ethanesulfonic acid)], BES [N,N-bis(2-hydroxyethyl)2-aminoethanesulfonic acid], BIS-TRIS [bis(2-hydroxyethyl)iminotris-(hydroxymethyl)methane; 2-bis(2-hydroxylethyl) amino-2-(hydroxymethyl-1,3-propanediol] and TES [(N-tris(hydroxymethyl)-methyl-2-aminoethanesulfonic acid); 2-((2-hydroxy-1,1-bis(-hydroxymethyl)ethyl) aminoethanesulfonic acid)].

The organic salts most commonly used to correct ionic strength are an alkali metal salt such as sodium sulfate, although other suitable salts that can be employed are well known to those skilled in the art.

The osmolality may be adjusted and set by the addition of an alkali metal salt such as sodium chloride. The level at which the osmolality is set will vary depending upon the particular adjusting salt and constituency of the diluent. Normally, with sodium chloride, the level at which the osmolality is set is 320±5 milliosmoles.

The pH is adjusted to 6.9±0.1 by use of a suitable base, for example, an alkali such as sodium hydroxide.

The proportions of the diluent constituents will vary depending upon the particular components selected but generally will fall within the following ranges:

|  | g/Liter |
| --- | --- |
| Organic buffer | about 8 to 12 |
| Diazolidinyl urea | about 1 to 5 |
| Water | balance |
| Osmolality, milliosmoles | 320 ± 5 |
| pH | 7.0 ± 0.1 |

A preferred diluent according to the invention is the following:

|  | g/Liter |
| --- | --- |
| Na₂SO₄ | 10 |
| NaCl | 4.3 |
| Diazolidinyl urea | 2.4 |
| PEG 8000 | 0.1 |
| Osmolality | 320 |
| pH | 7.0 |

The surfactant component optionally included in the diluent of the invention to prevent adsorption of platelets and red blood cells in hematology analyzing instruments can be of any suitable non-ionic, cationic or anionic surfactant. The preferred surfactants are selected from water-soluble polyalkylene ether glycols having the formula:

$$Z(OR')_nOH$$

wherein Z is H, alkyl, aryl or alkylaryl; R' is a divalent alkyl of 2 to 3 carbon atoms; n is greater or equal to 4 and water-soluble block copolymers of ethylene oxide and propylene oxide. In general the average molecular weight of these surfactants ranges from 400 to 10,000.

Examplary of suitable homopolymeric polyalkylene glycols are Polyethylene glycol 400, 600, 800, 1500, 4000, 6000, 8000 and Triton ® X 705 (polyethylene glycol p-isooctylphenyl ether).

Suitable block copolymers include the water-soluble block copolymers of ethylene oxide and propylene oxide having an average molecular weight of about 5,000 to 15,500. Such block copolymers are commercially available members of a family of nonionic surfactants commonly referred to as Pluronic ® polyols and supplied by the BASF Wyandotte Corporation. The Pluronic ® polyols are a series of block copolymers that consist of water-soluble poly(oxyethylene) groups at both ends of a water-insoluble poly(oxypropylene) chain. The first step in making the block copolymer is the controlled addition of propylene oxide to the two hydroxyl groups of a propylene glycol nucleus. The resulting polyoxypropylene glycol becomes water-insoluble at a molecular weight of 900. The hydrophobe is than tailored to the desired molecular weight and ethylene oxide added to sandwich the hydrophobic base between hydrophilic poly(oxyethylene) groups which are controlled in length.

The surfactant component, when present, is added in amounts sufficient to reduce or prevent the adsorption of blood platelets and red blood cells on the surfaces of the analyzing instruments. The optimum concentration of surfactant in the diluent varies depending on the particular reagents employed but usually falls in the range of about 0.05 to 0.5 g/liter.

The Lysing Agent

The lysing agent used with the novel diluent system of the invention can be any of the lytic agents heretofore employed for selectively dissolving red blood cells so as to permit separation and counting of white blood cells. Preferred amongst the lysing agents are one or more quaternary ammonium salts having surface active properties which have the structure:

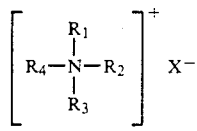

wherein $R_1$, $R_2$ and $R_3$ are lower alkyl groups of 1 to 6 carbon atoms; $R_4$ is a long chain alkyl group of, for example, 10 to 20 carbon atoms; and $X^-$ is salt forming groups such as a halide, phosphate or sulfate. In all instances, the concentration of the quaternary ammonium salt will be that effective to lyse the red blood cells without lysing of the white blood cells.

Examples of suitable quaternary ammonium salts are:
dodecyltrimethyl ammonium chloride,
dodecyltrimethyl ammonium bromide,
dodecyltrimethyl ammonium fluoride,
dodecyltrimethyl ammonium sulfate,
dodecyldimethylethyl ammonium chloride,
dodecyldimethylethyl ammonium fluoride,
dodecyldimethylethyl ammonium bromide, and
dodecyldimethylethyl ammonium sulfate.

The preferred lysing agent is a mixture of dodecyltrimethylcammonium chloride and tetradecyltrimethyl ammonium bromide in a weight ratio of 25 to 1.4.

A particularly preferred novel lysing agent of the invention comprises an aqueous solution of one or more of said quaternary ammonium salts in a volume concentration and total amount effective to lyse red blood cells in whole blood and differentiate white blood cells for counting, a lower alkanol in an amount that accelerates the shrinking effect of said quaternary ammonium salt and, optionally, a chromagen-forming agent such as an alkali metal cyanide. The preferred chromagen-forming agent is potassium cyanide.

The preferred lower alkanols are those having 2 to 4 carbons with isopropanol being preferred. In general, the concentration of alkanol in the lysing reagent is about 14 to 55 g/liter.

A particularly preferred lysing agent comprises:

|   | g/Liter |
|---|---|
| 1. Dodecyltrimethyl ammonium | 25.0 |

| | g/Liter |
|---|---|
| chloride | |
| 2. Tetradecyltrimethyl ammonium bromide | 1.40 |
| 3. KCN | 0.75 |
| 4. Isopropyl alcohol | 14.0 |

The following examples are given to further illustrate the present invention.

EXAMPLE I

This experiment was conducted to illustrate the effect of quaternary ammonium salt surfactants on white cell shrinking. Six aqueous lysing reagents (a) through (e) were prepared wherein the concentration of a mixture of dodecyltrimethyl ammonium chloride and tetradecyltrimethyl ammonium bromide was varied as shown in FIG. 1. The lysing reagent also contained 0.3 g/l KCN. A diluent system comprising

|   | g/Liter |
|---|---|
| 1. $Na_2SO_4$ | 10.0 |
| 2. NaCl | 4.3 |
| 3. HEPES* | 1.4 |
| 4. DU** | 0, 0.5 |
| 5. PEG 8000 | 0.1 |

*N-2hydroxyethylpiperazine-N'-2-ethanesulphonic acid
**diazolidinyl urea was also prepared.

Using a Sequoia-Turner 1600, samples of whole blood and the diluent system were fed into the counting bath of the instrument and the lysing reagent introduced. The histogram obtained with each concentration of quaternary ammonium salt are shown in FIG. 1 which shows the effect of the lysing agent concentration on the position of the white blood cells. The results in FIG. 1 demonstrate that as the concentration of lysing agent increases this causes the granulocytes and lymphocytes to move to the left, i.e., they are decreasing in size.

EXAMPLE II

In this example a mixture of 20 grams/l of dodecyltrimethyl ammonium bromide and 2.0 g/l of tetradecyltrimethyl ammonium bromide was used as the lysing agent. The diluent employed was similar to that employed in Example I except that concentrations of diazolidinyl urea was varied from 0%, 0.5%, 0.75%, 1.0%, 1.5% and 2.0%. Histograms were obtained as in Example I and are reported in FIG. 2 which show the effect of diazolidinyl urea on the position of the white blood cells.

Figure 2:
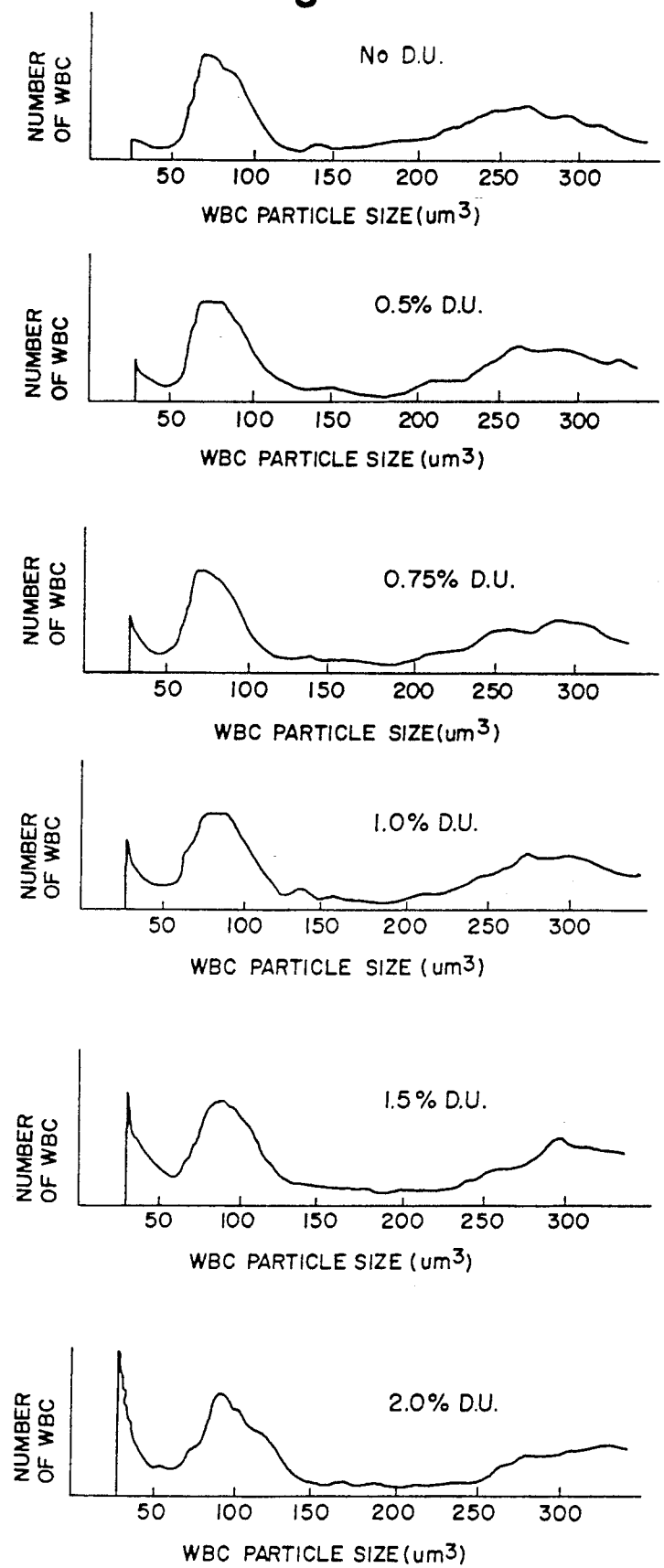
FIG. 2 demonstrates that increasing the concentration of diazolidinyl urea moves the white blood cells to the right, that is, stabilizes the white blood cells against the shrinking effect of the lysing agent.

The results of FIG. 2 demonstrate that increasing the concentration of diazolidinyl urea moves the white blood cells to the right, that is, the diazolidinyl urea stabilizes the white blood cells against the shrinking effect of the quaternary ammonium surfactant.

EXAMPLE III

Example II was repeated but using as the lysing agent 38 or 48 g/l of dodecyltrimethyl ammonium chloide and 2.0 g/l tetradecyltrimethyl ammonium bromide. The histograms obtained are reported in FIG. 3 which shows the effects of diazolidinyl urea on lysing agents containing higher concentrations of quaternary ammonium surfactants.

Figure 3:
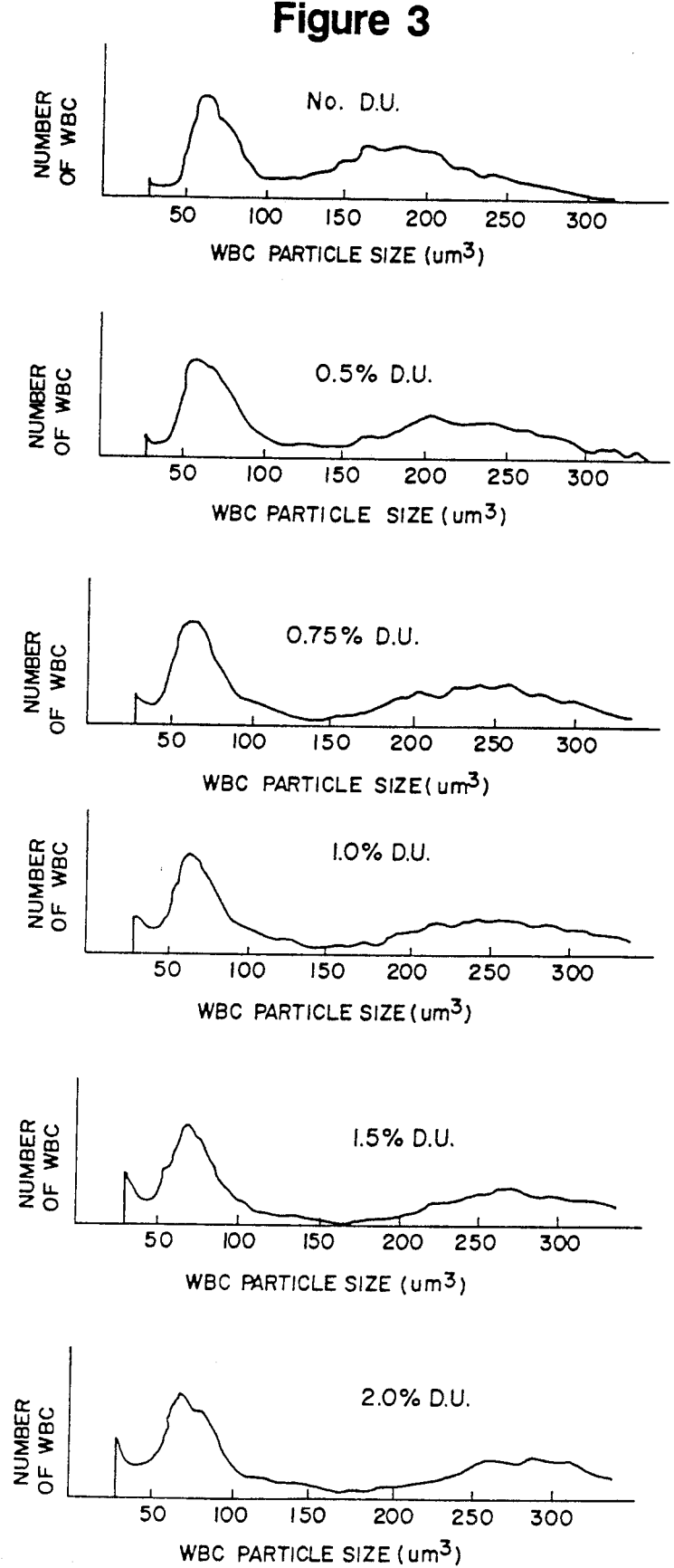
FIG. 3 and FIG. 4 demonstrate that the addition of diazolidinyl urea stabilizes the shrinking effect even at higher concentrations.
Figure 4:
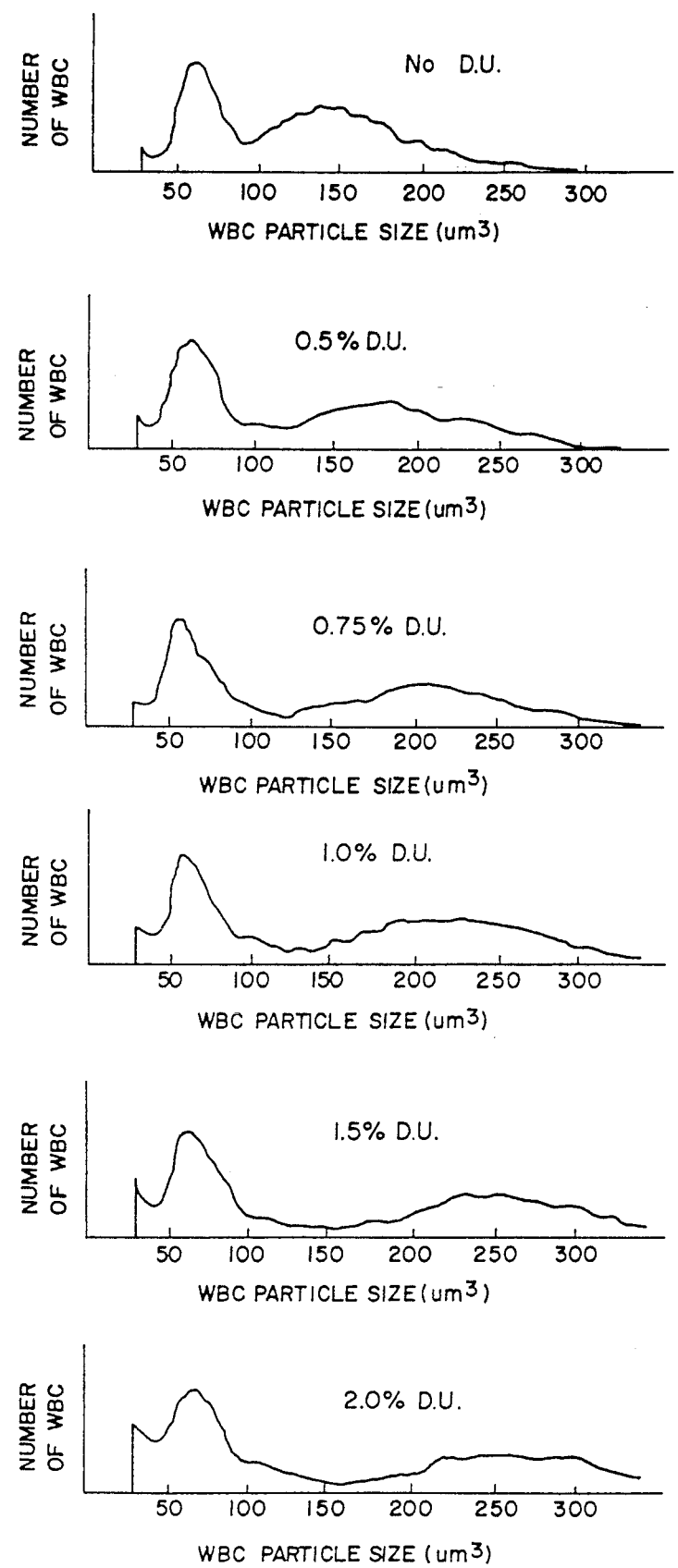

The results of FIG. 3 FIG. 4 demonstrate that the addition of diazolidinyl urea still stabilizes the shrinking effect of the lysing agent even at higher concentrations.

EXAMPLE IV

Example I was repeated but including either 0%, 2.8% or 11.0% isopropy alcohol as the lysing reagent. The histogram obtained reports the effects of isopropyl alcohol on the position of white blood cells and shows that isopropyl alcohol causes shrinking.

It is claimed:

1. In a method for the differentiation of white blood cells in whole blood using a differential hematology analyzing instrument wherein a whole blood sample diluted with a diluent containing a white blood cell stabilizer is mixed with a lysing agent to lyse the red blood cells and differentiate said white blood cells for counting by said instrument, the improvement comprising using as said white blood stabilizer diazolidinyl urea in an amount sufficient to stabilize said white blood cells against shrinkage during said lysis.

2. The improvement according to claim 1 wherein said diluent agent includes a surfactant glycol in an amount sufficient to reduce adsorption of blood platelets and red blood cells on surfaces of said hematology analyzing instruments.

3. The improvement according to claim 2 wherein the surfactant is a water-soluble polyalkylene ether glycol having the structure:

$$Z(OR')_nOH$$

wherein Z is H, alkyl, aryl or alkylaryl; R' is a divalent alkyl of 2 to 3 carbon atoms; n is greater or equal to 4; and block copolymers of ethylene oxide and propylene oxide.

4. The improvement according to claim 1 wherein the lysing reagent comprises one or more quaternary ammonium salts.

5. The improvement of claim 4 wherein the lysing agent is a mixture of dodecyltrimethyl ammonium chloride and tetradecyltrimethyl ammonium bromide.

6. The improvement of claim 4 wherein the lysing reagent includes a lower alkanol in an amount that accelerates the shrinking effect of said quaternary ammonium salt.

7. The improvement of claim 6 wherein the lower alkanol is isopropyl alcohol.

* * * * *